United States Patent [19]
Ono et al.

[11] Patent Number: 5,976,070
[45] Date of Patent: Nov. 2, 1999

[54] SIGNAL CABLE OF A VIDEO ENDOSCOPE PROVIDED WITH A SOLID STATE IMAGE PICK-UP DEVICE

[75] Inventors: Mitsunobu Ono, Tokyo; Masanao Murata, Tokorozawa, both of Japan

[73] Assignee: Olympus Optical Co., Ltd., Tokyo, Japan

[21] Appl. No.: 08/956,621

[22] Filed: Sep. 29, 1997

[30] Foreign Application Priority Data

Feb. 27, 1997 [JP] Japan ................................. 9-044409

[51] Int. Cl.$^6$ ....................................................... A61B 1/04
[52] U.S. Cl. .......................................... 600/110; 174/113 R
[58] Field of Search .................................. 600/110, 109, 600/130; 174/27, 28, 113 R

[56] References Cited

U.S. PATENT DOCUMENTS

| | | | |
|---|---|---|---|
| 4,745,470 | 5/1988 | Vabe et al. ............................... | 600/130 |
| 5,418,878 | 5/1995 | Sass et al. ................................ | 385/101 |
| 5,491,299 | 2/1996 | Naylor et al. ........................ | 174/113 R |
| 5,569,158 | 10/1996 | Suzuki et al. ............................ | 600/110 |
| 5,659,152 | 8/1997 | Horie et al. .......................... | 174/113 R |
| 5,770,820 | 6/1998 | Nelson et al. ....................... | 174/113 R |
| 5,834,697 | 10/1998 | Baker et al. ......................... | 174/113 R |

FOREIGN PATENT DOCUMENTS

| | | |
|---|---|---|
| 138402 | 9/1989 | Japan . |
| 184854 | 7/1995 | Japan . |

*Primary Examiner*—John P. Leubecker
*Attorney, Agent, or Firm*—Kenyon & Kenyon

[57] ABSTRACT

A signal cable for transmitting a plurality of signals is applied to a video endoscope having a solid state image pick-up device. Signal lines for transmitting substantially the same signals of the plurality of signals are combined and stranded into a stranded line. The stranding pitch of the stranding line is different from that of a stranding line for transmitting other signals.

11 Claims, 9 Drawing Sheets

FIG. 8

| TYPE | LOGIC OF SCOPE ID SIGNAL |
|---|---|
| FIRST VIDEO ENDOSCOPE | L |
| SECOND VIDEO ENDOSCOPE | H |

FIG. 9

| TYPE | CREST VALUE OF CCD DRIVING SIGNAL($\phi$H) | ABSOLUTE MAXIMUM RATED VALUE ($\phi$H) |
|---|---|---|
| FIRST VIDEO ENDOSCOPE | 8Vp-p (0~8V) | 10V DC |
| SECOND VIDEO ENDOSCOPE | 5Vp-p (0~5V) | 7V DC |

FIG. 11

| TYPE | INSERTING PORTION LENGTH | CREST VALUE OF CCD DRIVING SIGNAL (φH) | ABSOLUTE MAXIMUM RATED VALUE (φH) | CREST VALUE OF DRIVING SIGNAL OUTPUTTED FROM CCU |
|---|---|---|---|---|
| VIDEO ENDOSCOPE D | 2m | 5Vp-p | 7V | 5V |
| VIDEO ENDOSCOPE E | 2m | 8Vp-p | 10V | 8V |
| VIDEO ENDOSCOPE F | 10m | 8Vp-p | 10V | 12V |

FIG. 12

| TYPE | SCOPE ID SIGNAL A | SCOPE ID SIGNAL B |
|---|---|---|
| VIDEO ENDOSCOPE D | L | L |
| VIDEO ENDOSCOPE E | L | H |
| VIDEO ENDOSCOPE F | H | L |
| NO VIDEO ENDOSCOPE CONNECTED | H | H |

FIG. 13

| SCOPE ID SIGNAL A | SCOPE ID SIGNAL B | CORD A | CORD B |
|---|---|---|---|
| L | L | H | H |
| L | H | H | L |
| H | L | L | L |
| H | H | H | H |

SIGNAL CABLE OF A VIDEO ENDOSCOPE PROVIDED WITH A SOLID STATE IMAGE PICK-UP DEVICE

FIELD OF THE INVENTION

The present invention relates to a signal cable inserted through an inserting portion of a video endoscope. The signal cable prevents a degradation of a signal transmitted via the signal cable and can minimize the diameter of an inserting portion of the video endoscope.

BACKGROUND INFORMATION

In the medical field, a medical video endoscope has been broadly used. The medical video endoscope has an inserting portion to be inserted in a body cavity for observing an organ from the inside of the body cavity, and/or a treating instrument inserting channel through which a treating instrument is inserted to perform various types of treatments for the organ.

In the industrial field, an industrial video endoscope has also been broadly used. The industrial video endoscope can observe and inspect a scratch or a corrosion inside an object, such as a boiler, a turbine, an engine, a chemical plant, or the like.

Particularly, an inserting portion of a video endoscope used for inspecting a jet engine of an aircraft is desired to be thin, so that the inserting portion can easily be inserted in the engine which has a complicated structure.

Generally, the video endoscope is provided at the distal end of its inserting portion with a solid state image pick-up device which functions as an image pick-up means and includes, for example, a charge-coupled device (CCD). A signal cable for transmitting a driving signal of the charge-coupled device is inserted through the inserting portion of the video endoscope.

The signal cable usually includes a bundle of ten-odd signal lines. Namely, the charge-coupled device is connected to the ten-odd signal lines in order to drive the charge-coupled device and to output the image signal of the charge-coupled device. The ten-odd wires constitute the signal cable for transmitting the driving signal and the like of the charge-coupled device. Signals having different frequencies are transmitted respectively to the ten-odd signal lines constituting the signal cable.

Since the signal cable is inserted through a long inserting portion of the video endoscope, the signal cable has a long length proportional to the length of the inserting portion.

When the signal cable is long, it is necessary to stabilize the signal transmitted via the signal cable. Therefore, it has been common to use as the signal line a coaxial cable having a shield structure for preventing the influence of electrical interference and outside noise.

However, since the coaxial cable has the shield structure, the outer size of the coaxial cable is larger than that of a non-shielded signal line which has no shield structure.

When a plurality of coaxial cables are bundled and used as a signal cable of a video endoscope, it is a problem that the outer size of the signal cable becomes considerably large, thereby thickening the inserting portion of the video endoscope through which the signal cable is inserted.

In order to solve this problem, Japanese Laid-Open Patent Application Publication No. 7-184854 describes a video endoscope whose inserting portion can be thin.

In this video endoscope, a coaxial cable which can avoid noise influence is used for transmitting a high-frequency signal, and a non-shielded signal line is used for transmitting a direct current signal. In this way, depending on what kind of signal is transmitted, different types of signal lines are used, thereby minimizing the outer size of the signal cable which includes a bundle of a plurality of signal lines.

However, in the video endoscope disclosed in Japanese Laid-Open Patent Application Publication No. 7-184854, the outer size of the signal cable is limited, depending on the number of the coaxial cables. That is, unless the number of the coaxial cables used is decreased, the signal cable cannot be thinner.

In order to reduce the outer size of the signal cable, all coaxial cables used for the signal cable may merely be replaced with non-shielded signal lines.

However, because signals having various frequencies are transmitted through the signal lines, electrical interference between signals in the signal cable may occur and noise from a signal line may affect another signal line. As a result, the transmission characteristics of the signal cable are deteriorated so that the charge-coupled device will operate erroneously or cannot be driven sufficiently. Thus, the quality of the image picked up by the charge-coupled device will be deteriorated.

Therefore, in Japanese Laid-Open Patent Application Publication No. 7-184854, the minimization of the outer diameter of the inserting portion of the video endoscope has a limit. Consequently, this cannot provide a video endoscope having a thinner inserting portion.

SUMMARY OF THE INVENTION

In view of the above problems, an object of the present invention is to minimize an outer size of a signal cable used for a video endoscope without deteriorating its transmission characteristics.

Another object of the present invention is to minimize an outer diameter of an inserting portion of a video endoscope by using a signal cable having a small outer size without deteriorating its transmission characteristics.

BRIEF DESCRIPTION OF THE DRAWINGS

FIG. 8 shows a table showing an example of logic of scope ID signals of two video endoscopes.

FIG. 9 shows a table illustrating rated crest values and absolute maximum rated values of driving pulses for the two video endoscopes.

FIG. 11 shows a table illustrating specifications of three video endoscopes.

FIG. 12 shows a table illustrating relations between the video endoscopes and scope ID signals.

FIG. 13 shows a table illustrating relations between inputs to and outputs from a decoder.

DETAILED DESCRIPTION OF THE PREFERRED EMBODIMENTS

Figure 1:
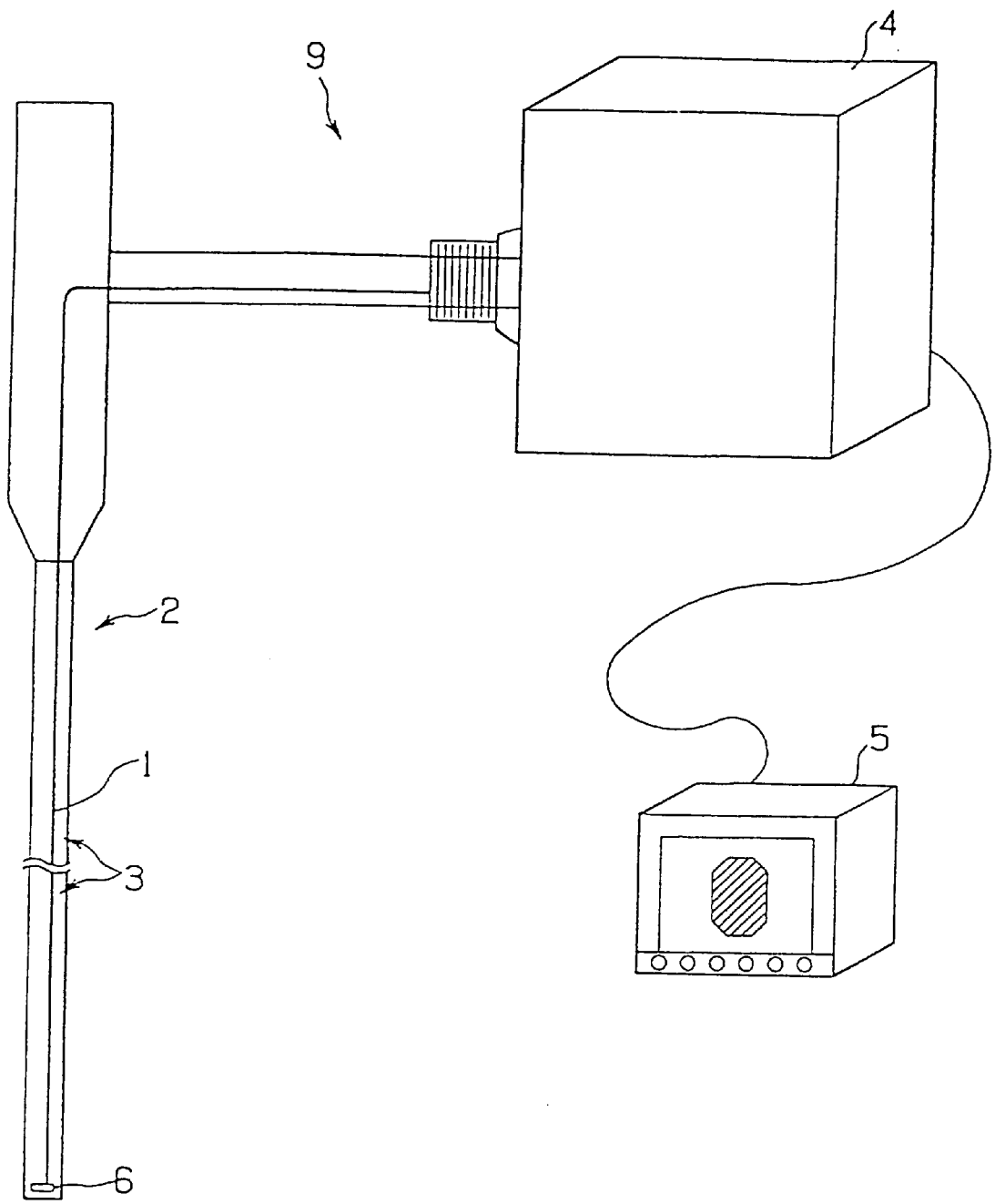
FIG. 1 shows a schematic view of a video endoscope system according to a first embodiment of the present invention.

As shown in FIG. 1, a composite signal cable 1 for a video endoscope 2 according to the present invention is inserted through an inserting portion 3 of the video endoscope 2.

A video endoscope system 9 mainly includes the video endoscope 2, a camera control unit 4 (CCU), and a television monitor 5.

A solid state image pick-up device functioning as an image pick-up means, for example, a charge-coupled device 6 is included in a distal end portion of the inserting portion 3 of the video endoscope 2.

The signal cable 1 connects the charge-coupled device 6 to the camera control unit 4.

The camera control unit 4 generates a driving signal for driving the charge-coupled device 6. The signal cable 1 transmits the generated driving signal to the charge-coupled device 6 to drive the charge-coupled device 6.

A lens (not shown) forms an optical image on an image pick-up surface of the charge-coupled device 6. The charge-coupled device 6 photoelectrically converts the optical image formed on the charge-coupled device 6 into an electrical signal. The electrical signal as an image output signal is transmitted to the camera control unit 4 via the signal cable 1.

The image output signal transmitted to the camera control unit 4 is processed by the camera control unit 4 into a video signal which can be displayed on the television monitor 5. The camera control unit 4 transmits the video signal to the television monitor 5. The television monitor 5 displays as an endoscopic image an object image formed on the charge-coupled device 6.

Figure 2:
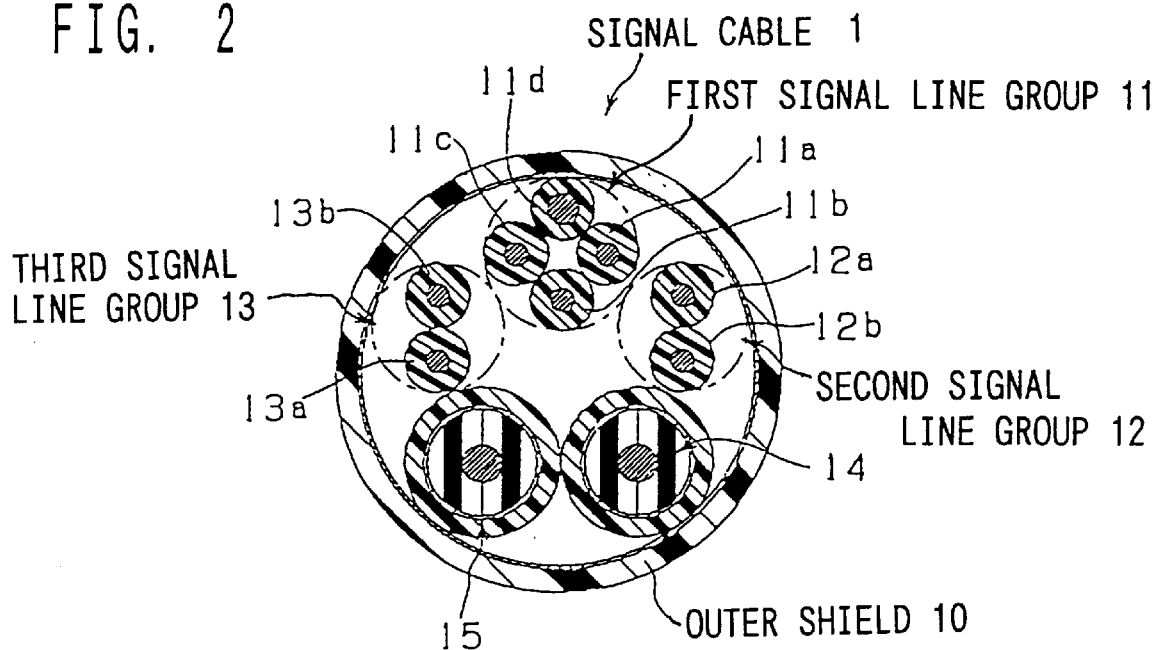
FIG. 2 shows a cross-sectional view illustrating the arrangement of a plurality of signal lines constituting a composite signal cable according to the first embodiment.

As shown in FIG. 2, the composite signal cable 1 includes an outer shield 10 and a plurality of signal lines inserted through the outer shield 10. The plurality of signal lines include a plurality of coaxial cables and a plurality of non-shielded signal lines.

The outer shield 10 has a known shield structure which shields electromagnetic waves generated by the signal lines positioned inside the outer shield 10, so that the electromagnetic waves will not leak outside.

The signal lines inserted through the outer shield 10 include driving signal lines (driving lines) for driving the charge-coupled device 6, an image signal line (image line) for transmitting the image signal outputted from the charge-coupled device 6, and power source lines.

The driving lines include signal lines for driving signals for vertical transfer of the charge-coupled device 6 (φV signal lines) and signal lines for driving signals for horizontal transfer of the charge-coupled device 6 (φH signal lines).

The φV signal lines include a first φV signal line 11a, a second φV signal line 11b, a third φV signal line 11c, and a fourth φV signal line 11d. These four φV signal lines are inserted through the outer shield 10.

The φH signal lines include a first φH signal line 12a, and a second φH signal line 12b. These two φH signal lines are also inserted through the outer shield 10.

On the other hand, the power source lines include a VDD line 13a and a VL line 13b for driving the charge-coupled device 6, which are also inserted through the outer shield 10.

The image line is a signal line 14 for the image output signal ($V_{out}$ signal line). The $V_{out}$ signal line 14 is also inserted through the outer shield 10.

Further, the driving lines also include a signal line 15 for a reset pulse for an output gate of the charge-coupled device 16 (φR signal line). The φR signal line is also inserted through the outer shield 10.

The frequencies of the signals transmitted by the $V_{out}$ signal line 14 and the φR signal line 15 are approximately 100 MHz, and disturbances of these signals greatly affect the quality of the endoscopic image. Therefore, in order to prevent the signals from being affected by an electrical interference or a noise, coaxial cables having shield structures are used as the $V_{out}$ signal line 14 and the φR signal line 15 which transmit these signals.

On the other hand, non-shielded signal lines are used as the other driving lines and the power source lines.

The first, second, third, and fourth φV signal lines 11a, 11b, 11c, and 11d are the signal lines for transmitting the driving signals for vertical transfer. Thus, all the signals transmitted through the signal lines 11a, 11b, 11c, and 11d have the same frequency. Accordingly, as shown by a dash-dotted line in FIG. 2, the first, second, third, and fourth φV signal lines 11a, 11b, 11c, and 11d are combined into a first signal line group 11 consisting of the signal lines which transmit the driving signals for vertical transfer.

Similarly, since the first and second φH signal lines 12a and 12b are the signal lines for transmitting the driving signals for horizontal transfer, all the signals transmitted through the signal lines 12a and 12b have the same frequency. Thus, as shown by a dash-dotted line in FIG. 2, the first and second φH signal lines 12a and 12b are combined into a second signal line group 12 consisting of the signal lines which transmit the driving signals for horizontal transfer.

Further, since the VDD line 13a and the VL line 13b are the power source lines, the signals transmitted by these lines are direct currents and hence do not have different frequencies. Accordingly, as shown by a dash-dotted line in FIG. 2, the VDD line 13a and the VL line 13b are combined into a third signal line group 13 consisting of the signal lines which provide power.

Figure 3:
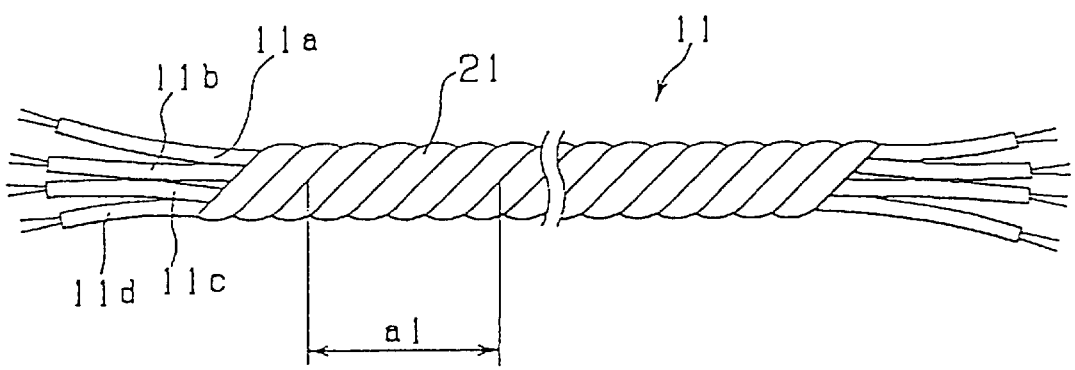
FIG. 3 shows a partially omitted view illustrating an example of a signal line group constituting a part of the signal cable according to the first embodiment.

As shown in FIG. 3, the signal lines of the first signal line group 11 are bundled and stranded to form a first stranded line 21. The number of turns per unit length (stranding pitch) of the first stranded line 21 is a1.

Although not shown, the signal lines of the second signal line group 12 and the third signal line group 13 are bundled and stranded to form a second stranded line and a third stranded line. The number of turns per unit length of the second stranded line is a2, and that of the third stranded line is a3.

Namely, the numbers of turns per unit length of the first, second, and third stranded lines are different.

Functions and effects of the composite signal cable 1 as described above are also described below.

As described above, the $V_{out}$ signal line 14 and the φR signal line 15 for transmitting a high-speed clock of a high frequency are inserted through the outer shield 10 which constitutes the complex signal cable 1. Since coaxial cables are used for the $V_{out}$ signal line 14 and the φR signal line 15, these transmission lines are electrically shielded from their surroundings.

The first, second, third, and fourth φV signal lines 11a, 11b, 11c, and 11d, and the first and second φH signal lines 12a and 12b are driving lines for transmitting the driving signals having frequency bands different from those of the high-speed clock. A non-shielded signal line is used for each driving line.

The VDD line 13a and the VL line 13b are the power source lines for providing direct currents. Non-shielded signal lines are also used for the power source lines.

In this way, the driving lines and the power source lines formed of the non-shielded signal lines are inserted through the outer shield 10 of the composite signal cable 1. Thus, the outer diameter of the composite signal cable 1 is small.

Moreover, the non-shielded signal lines which transmit the signals having the same frequency or similar waveform patterns are combined into a signal line group. In this way, first, second, and third signal line groups 11, 12, and 13 are formed. The signal lines in each signal line group are stranded to form a stranded line. Thus, first, second, and third stranded lines are formed. The numbers of turns per unit length of the first, second, and third stranded lines are different.

Hence, for example, the noise from the second stranded line formed by the first and second φH signal lines 12a and 12b in the second signal line group 12 will enter neither the first stranded line formed by the first to fourth φV signal lines 11a to 11d in the first signal line group 11, nor the third stranded line formed by the VDD line 13a and the VL line 13b in the third signal line group 13.

In this way, electrical interference between the stranded lines which constitute different signal line groups are reduced. That is, even when the non-shielded signal lines are used in the composite signal cable 1, the transferring characteristics of the signal cable 1 will not be sacrificed so that the charge-coupled device 6 can be operated stably.

In summary, a plurality of driving lines and power source lines are made of non-shielded signal lines. The non-shielded signal lines are divided into signal line groups in accordance with the frequencies and the waveform patterns of the signals to be transmitted by them. The signal lines in each signal line group are stranded to form a stranded line such that the numbers of turns per unit length of the respective stranded lines are different. In this way, the driving signal can be transmitted to the charge-coupled device 6 stably and the outer diameter of the composite signal cable 1 can be reduced.

Further, instead of using expensive coaxial cables for the signal lines for the driving signals for vertical and horizontal transfer of the charge-coupled device 6, low-cost non-shielded signal lines are used. Therefore, the number of coaxial cables inserted through the composite signal cable 1 is reduced, which can reduce the price of the signal cable 1.

Figure 4:
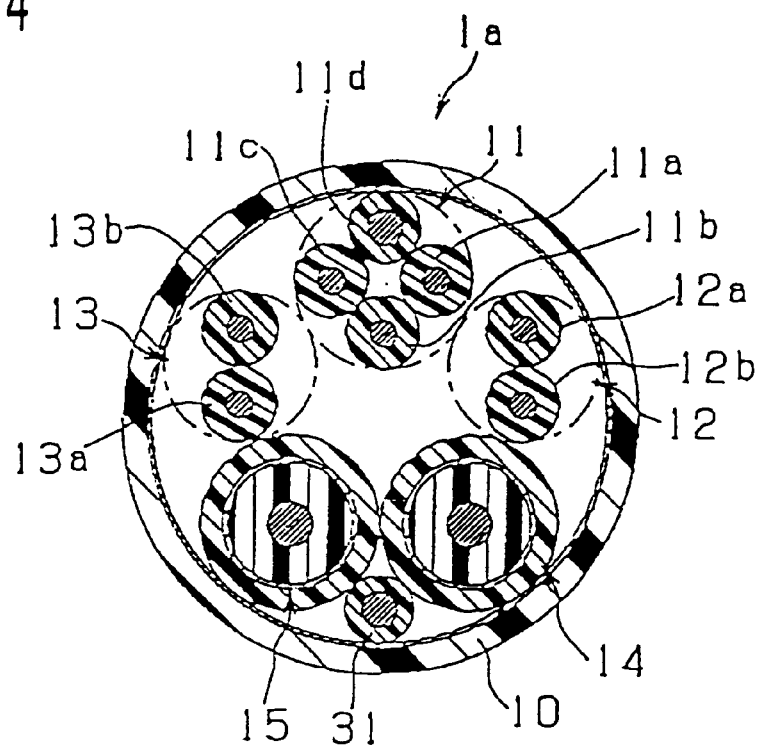
FIG. 4 shows a cross-sectional view illustrating the arrangement of a plurality of signal lines constituting a composite signal cable according to a second embodiment of the present invention.

Next, referring to FIG. 4, a second embodiment of the present invention will be described. FIG. 4 shows a cross-sectional view of another composite signal cable 1a, through which a plurality of signal lines are also inserted.

This embodiment applies to a case in which there is a signal line which cannot constitute a signal line group to form a stranded line because it does not transmit any signal which is the same as the signals transmitted by the other signal lines.

Members which are the same as those of the first embodiment will be given the same numerals as those of the first embodiment, and their descriptions will be omitted.

As shown in FIG. 4, a signal line 31 for an electronic shutter pulse (SUB signal line) is inserted through the outer shield 10 of the composite signal cable 1a. The SUB signal line 31 is a driving signal line which transmits a signal for controlling an electronic shutter function of the charge-coupled device 6. A non-shielded signal line is used for the SUB signal line 31.

The SUB pulse signal transmitted by the SUB signal line 31 has a high crest value only when the electronic shutter of the charge-coupled device 6 is controlled.

When a noise of the SUB pulse is mixed into, for example, a first φV signal line 11a, a malfunction of the charge-coupled device 6 may occur. Namely, the SUB pulse may greatly influence on other driving lines, such as the first to fourth φV signal lines 11a–11d and first and second φH signal lines 12a and 12b. Therefore, it is necessary to prevent the influence of the noise derived from the SUB pulse transmitted by the SUB signal line 31.

Therefore, as shown in FIG. 4, the SUB signal line 31 made of a non-shielded signal line is arranged in a space formed by the outer shield 10, and a $V_{out}$ signal line 14 and a φR signal line 15 which are made of coaxial cables. That is, the SUB signal line 31 is surrounded by the two coaxial cables (the $V_{out}$ signal line 14 and the φR signal line 15) and the outer shield 10 to spatially separate and electrically shield the SUB signal line 31 from the other driving lines (the first to fourth φV signal lines 11a to 11d and the first and second φH signal lines 12a and 12b) and the power source lines (a VDD line 13a and a VL line 13b).

Functions and effects of the composite signal cable 1a structured in this way will be described.

As described above, the SUB signal line 31 made of a non-shielded signal line cannot be combined with other signal lines because it transmits a special signal compared with other signals. Accordingly, the SUB signal line 31 is surrounded by the outer shield 10, and the $V_{out}$ signal line 14 and the φR signal line 15 made of coaxial cables.

Thus, even when a pulse having a high crest value is transmitted to the SUB signal line 31 and noise is generated during the electronic shutter operation of the charge-coupled device 6, the noise is shielded and does not leak outside because of the shield structure formed by the coaxial cables 14 and 15 and the outer shield 10. Hence, the noise generated by the SUB signal line 31 will not be mixed into the other driving lines or the power source lines so that malfunction of the charge-coupled device 6 can be prevented.

In summary, the SUB signal line 31 is made of a non-shielded signal line instead of a coaxial cable, and is surrounded by the outer shield 10 having a shield structure, and two coaxial cables (the $V_{out}$ signal line 14 and the φR signal line 15). In this way, without providing inside the composite signal cable 1a an additional member for shielding the SUB signal line 31, it is possible to reduce the diameter of the signal cable 1a with the SUB signal line 31 being spatially separated and electrically shielded from the other driving lines or the power source lines.

Further, since the SUB signal line 31 is positioned in the space formed by the outer shield 10, the $V_{out}$ signal line 14, and the φR signal line 15, the space in the signal cable 1a can be efficiently used, which also contributes to reducing the outer diameter of the signal cable 1a.

Other functions and effects of the second embodiment are the same as those of the first embodiment.

Figure 5:
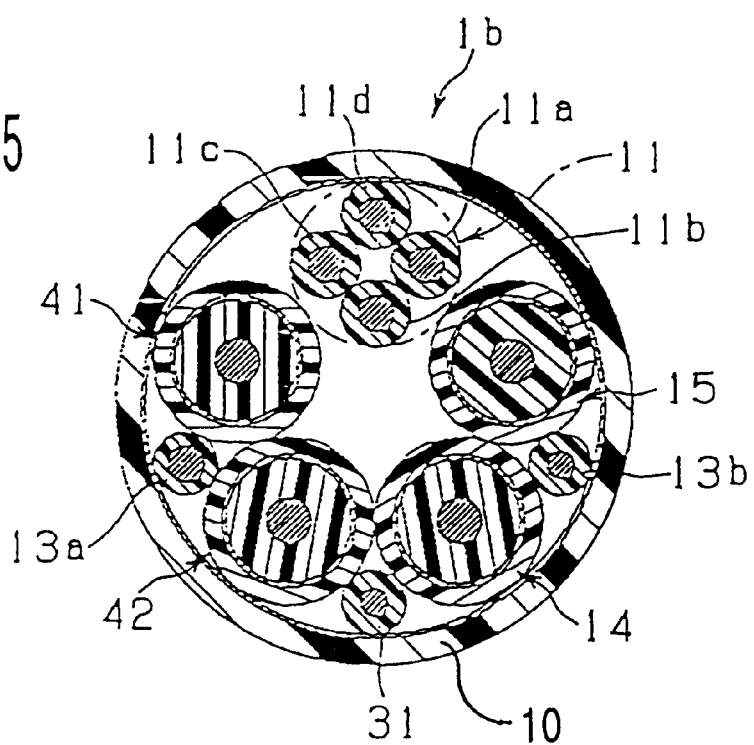
FIG. 5 shows a cross-sectional view illustrating the arrangement of a plurality of signal lines constituting a composite signal cable according to a third embodiment of the present invention.

Next, referring to FIG. 5, a third embodiment of the present invention will be described. FIG. 5 shows a cross-sectional view of another composite signal cable 1b, through which a plurality of signal lines are also inserted.

This embodiment is provided for the case in which a high-speed clock signal of a high frequency is used as a driving signal for horizontal transfer of the charge-coupled device.

As shown in FIG. 5, a first φH signal line 41 and a second φH signal line 42 for transmitting driving signals for horizontal transfer of the charge-coupled device are made of coaxial cables. Thus, when a high-speed clock signal is used for the driving signals for horizontal transfer of the charge-coupled device, electromagnetic waves radiated outward from the composite signal cable 1b can be reduced.

The coaxial cables inside an outer shield 10 are a $V_{out}$ signal line 14 and a φR signal line 15 as well as the first and second φH signal lines 41 and 42. Namely, four coaxial cables are positioned in the outer shield 10.

Therefore, as shown in FIG. 5, it is possible to arrange a VDD line 13a in a space formed by the outer shield 10 and the first and second φH signal lines 41 and 42; an SUB signal line 31 in a space formed by the outer shield 10, the second φH signal line 42, and the $V_{out}$ signal line 14; and a VL line 13b in a space formed by the outer shield 10, the Vout signal line 14, and the φR signal line 15.

In this way, when the number of coaxial cables inside the outer shield 10 has to be increased, signal lines using non-shielded signal lines are positioned in the spaces formed by the outer shield 10 and two coaxial cables. Thus, the space in the cross-section of the composite signal cable 1b can be used efficiently to reduce the outer diameter of the signal cable 1b. Moreover, electrical interference on the signal lines made of non-shielded signal lines can be prevented by the shield structure of the outer shield 10 and the two coaxial cables surrounding the signal lines.

Incidentally, there has been a video endoscope system using a plurality of video endoscopes. In such a video endoscope system, in order to use the video endoscopes having respective charge-coupled devices which are different in their specifications, the camera control unit is provided with plural types of driving signal generating circuits for generating signals for driving the charge-coupled devices. For example, Japanese Laid-Open Utility Model Application Publication No. 1-138402 discloses such a video endoscope system.

In this video endoscope system, the camera control unit is provided with plural kinds of driving signal generating circuits. When a video endoscope is connected to the camera control unit, a driving signal appropriate for driving the charge-coupled device of the video endoscope is selected and outputted by a switching means. Thus, plural types of video endoscopes can be connected to the camera control unit.

On the other hand, technological advances of the charge-coupled devices used for the video endoscopes are rapid. The number of pixels of the charge-coupled device has increased from 140,000 successively to 180,000; 250,000; and 380,000. Further, the power consumed by the charge-coupled device has been reduced. The crest value of the voltage of the driving signal for driving the charge-coupled device has been reduced from 8 V to 5 V.

Therefore, for example, video endoscope A purchased three years uses a charge-coupled device having a driving frequency of 10 MHz, a φH driving signal crest value of 8 $V_{p-p}$, and an absolute maximum rated value of DC 10 V, while the video endoscope B purchased recently uses a charge-coupled device having a driving frequency of 14 MHz, a φH driving signal crest value of 5 $V_{p-p}$, and an absolute maximum rated value of DC 7 V.

Accordingly, video endoscopes A and B cannot be applied to the video endoscope system disclosed in Japanese Laid-Open Utility Model Application Publication No. 1-138402 because of the difference between the crest values of the driving signals for the charge-coupled devices, and the difference between the absolute maximum rated values.

For example, if video endoscope B in place of video endoscope A is connected to the camera control unit when the camera control unit is going to generate a driving signal appropriate to video endoscope A, a driving signal of 8 $V_{p-p}$, which exceeds the absolute maximum rated value of DC 7 V of the charge-coupled device incorporated in the video endoscope B, is inputted into the charge-coupled device of the video endoscope B so that the charge-coupled device of the video endoscope B will be damaged.

Therefore, there is demand for a camera control unit which can be connected to plural types of video endoscopes having respective charge-coupled devices which are different in their specifications, such as the crest values of the driving signals and the absolute maximum rated values.

The structure of a video endoscope system capable of meeting this demand will be described.

Figure 6:
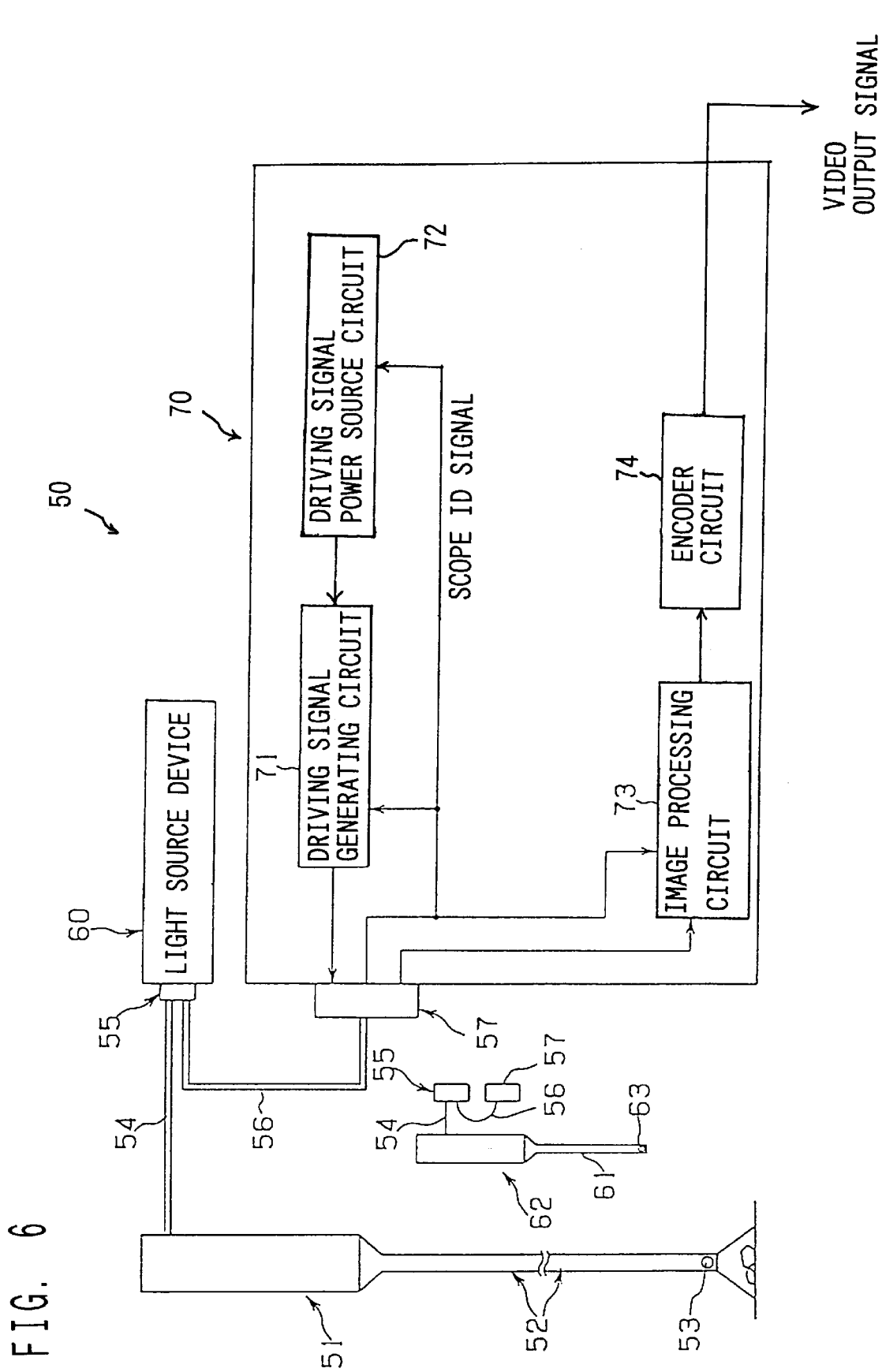
FIG. 6 shows a schematic view of a video endoscope system.

As shown in FIG. 6, a video endoscope system 50 includes a first video endoscope 51, a light source device 60 for supplying illumination light to the first video endoscope 51, and a camera control unit 70. The first video endoscope 51 has an inserting portion 52 provided in its distal end portion with a first charge-coupled device 53. A composite signal cable (not shown in FIG. 6) extends from the first charge-coupled device 53. This signal cable is one of the signal cables described in the above first to third embodiments and is inserted through a universal cord 54. The universal cord 54 is provided in its proximal end portion with a light guide connector 55, which is detachably connected to the light source device 60. An electric cable 56 extends from the light guide connector 55. The electric cable 56 is provided in its proximal end portion with a camera control unit connector 57, which is detachably connected to the camera control unit 70.

Thus, the first video endoscope 51 can be independent by detaching the light guide connector 55 and the camera control unit connector 57 from the light source device 60 and the camera control unit 70, respectively.

Further, the video endoscope 50 is provided with a second video endoscope 62 in addition to the first video endoscope 51. The second video endoscope 62 has an inserting portion 61 which is provided in its distal end portion with a second charge-coupled device 63 which is different from the first charge-coupled device 53 in their specifications.

Thus, in the video endoscope system 50, the first and second video endoscopes 51 and 62 can be connected to the camera control unit 70.

The camera control unit 70 contains a driving signal generating circuit 71, a driving signal power source circuit 72, an image processing circuit 73, and an encoder circuit 74. The driving signal generating circuit 71 generates driving signals for driving the first and second charge-coupled devices 53 and 63. The driving signal power source circuit 72 supplies power to the driving signal generating circuit 71. The image processing circuit 73 processes image signals outputted from the first and second charge-coupled devices 53 and 63.

The image signal outputted from the encoder circuit 74 is outputted as a video output signal from the camera control unit 70 to a television monitor (not shown).

The crest value of the driving signal for the first charge-coupled device 53 generated from the camera control unit 70 changes depending on the voltage outputted from the driving signal power source circuit 72.

A detailed structure of the driving signal generating circuit 71 is the same as that described in Japanese Laid-Open Utility Model Application Publication No. 1-138402. The driving signal generating circuit 71 has two driving signal generating circuits for the charge-coupled devices 53 and 63 of the two endoscopes 51 and 62. These driving signal generating circuits can generate driving signals having different pulse intervals corresponding to the different types of charge-coupled devices.

Figure 7:
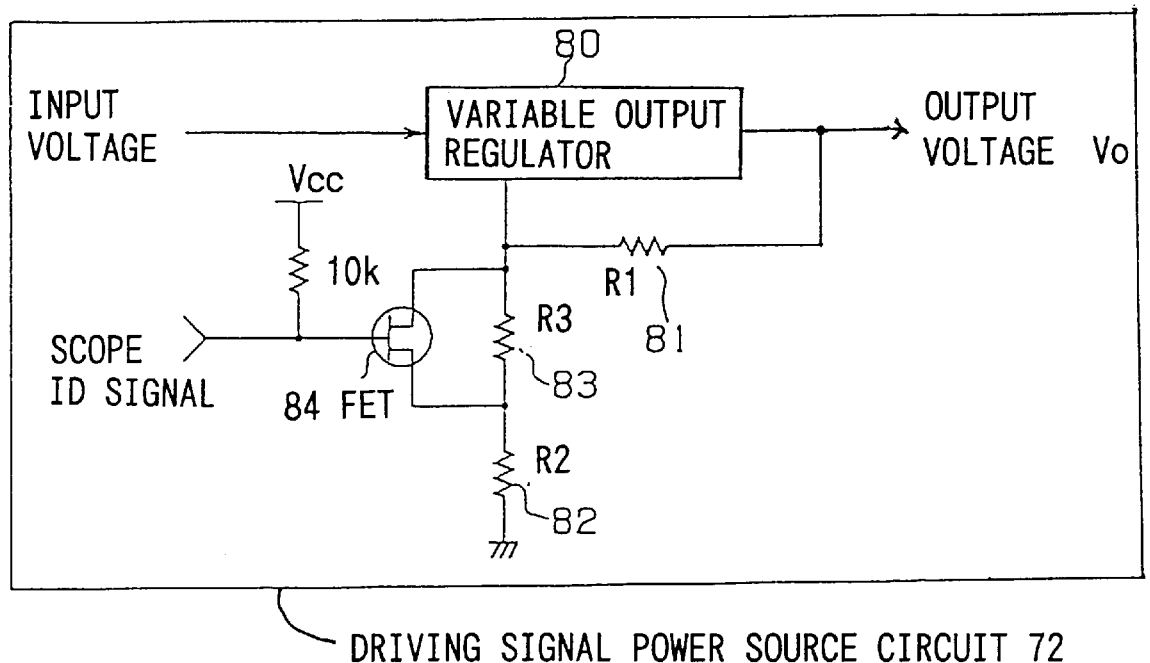
FIG. 7 is a circuit diagram of an example of a power source circuit for generating a driving signal which drives a solid state image pick-up device.

As shown in FIG. 7, the driving signal power source circuit 72 includes a variable output regulator 80, first to third resistors 81 to 83 for setting an output voltage of the variable output regulator 80, and a field-effect transistor (FET) 84.

A scope ID signal inputted to the driving signal power source circuit 72 shown in FIG. 7 is a signal for changing the output voltage of the variable output regulator 80. The scope ID signal is generated by the first and second video endoscopes 51 and 62 and supplied to the camera control unit 70 via the camera control unit connector 57.

As shown in FIG. 7, the input terminal of the scope ID signal is connected to a $V_{cc}$ via a resistor of 10 kΩ. Therefore, in FIG. 6, when the camera control unit connector 57 is not connected to the camera control unit 70, namely, when the first and second video endoscopes 51 and 62 are not connected to the camera control unit 70, the scope ID signal is at an "H" level.

As shown in FIG. 8, the scope ID signal of the first video signal 51 is at an "L" level, and the scope ID signal of the second video signal 62 is at the "H" level.

In FIG. 7, when the scope ID signal is at the "H" level, the field-effect transistor 84 turns on and the existence of the third resistor 83 is canceled.

Hence, the output voltage $V_o$ of the variable output regulator 80 is as follows:

$$V_o \approx 1.25(1+R2/R1)$$

On the other hand, when the scope ID signal is at the "L" level, the field-effect transistor 84 turns off and the current flows through the second resistor 83.

Thus, the output voltage $V_o$ of the variable output regulator 80 is as follows:

$$V_o \approx 1.25(1+(R2+R3)/R1)$$

Therefore, the output voltage $V_o$ of the variable output regulator 80 is lower when the scope ID signal is at the "H" level than at the "L" level.

As shown in FIG. 9, the first charge-coupled device 53 of the first video endoscope 51 has a φH driving signal crest value of 8 $V_{p-p}$ and an absolute maximum rated value of DC 10 V. The second charge-coupled device 63 of the second video endoscope 62 has a φH driving signal crest value of 5 $V_{p-p}$ and an absolute maximum rated value of DC 7 V.

In the driving signal power source circuit 72 shown in FIG. 7, the constant values of the first to third resistors 81 to 83 are determined so that they will satisfy the relations shown in FIGS. 8 and 9.

An operation of the video endoscope system 50 as described above will be described.

When neither the first video endoscope 51 nor the second video endoscope 62 is connected to the camera control unit 70 of the video endoscope system 50, the scope ID signal is at is at the "H" level. Thus, the φH driving signal outputted from the camera control unit 70 has a crest value of 5 $V_{p-p}$.

Suppose the first video endoscope 51 or the second video endoscope 62 is connected to the camera control unit 70 in this state.

Whether the first video endoscope 51 or the second video endoscope 62 is connected to the camera control unit 70, the scope ID signal ensures the input into the connected video endoscope of only a driving signal having a crest value which is smaller than or equal to the absolute maximum rated value of the charge-coupled device provided in the video endoscope.

In this way, when no video endoscope is connected to the camera control unit 70, the camera control unit 70 outputs a driving signal corresponding to the charge-coupled device having an absolute maximum rated value which is the smallest of all the absolute maximum rated values of the charge-coupled devices used in the video endoscopes to be connected to the camera control unit 70.

When a video endoscope is connected to the camera control unit 70, the camera control unit 70 detects the scope ID signal of the video endoscope and generates a driving signal appropriate for the detected video endoscope. Accordingly, when a video endoscope is connected to the camera control unit 70, irrespective of the specification of the charge-coupled device of the video endoscope, the crest value of the driving signal outputted from the camera control unit 70 to the video endoscope is lower than the absolute maximum rated value of the charge-coupled device without fail. Thus, the charge-coupled device to be driven can be protected.

Although this embodiment deals with only the φH driving signal as a driving pulse for the charge-coupled device, the same structure may be used for the φV driving signal and the φR driving signal.

Referring to FIGS. 10 to 13, another example of the camera control unit will be described.

There are three types of video endoscopes connectable to the camera control unit 70. As shown in FIG. 11, the three types are video endoscopes D, E, and F.

The charge-coupled device used in video endoscope D has a φH driving signal crest value of 5 V and an absolute maximum rated value of DC 7 V, and the inserting portion of video endoscope D has a length of 2 m. The crest value of the driving signal when outputted from the camera control unit 70 for driving video endoscope D is 5 V.

Video endoscope E is provided with a charge-coupled device having a specification different from that of the charge-coupled device of video endoscope D. The charge-coupled device of video endoscope E has a φH driving signal crest value of 8 V and an absolute maximum rated value of DC 10 V, and the inserting portion of video endoscope E has a length of 2 m. The crest value of the driving signal when outputted from the camera control unit 70 for driving video endoscope E is 8 V.

Video endoscope F is provided with a charge-coupled device having the same specification as that of the charge-coupled device of video endoscope E. However, the length of the inserting portion of video endoscope F is 10 m. The crest value of the driving signal when outputted from the camera control unit 70 for driving video endoscope F is 12 V. The crest value when outputted is large because the signal cable inserted through the inserting portion of video endoscope F is long so that the apparent load on the signal cable viewed from the camera control unit is large.

Figure 10:
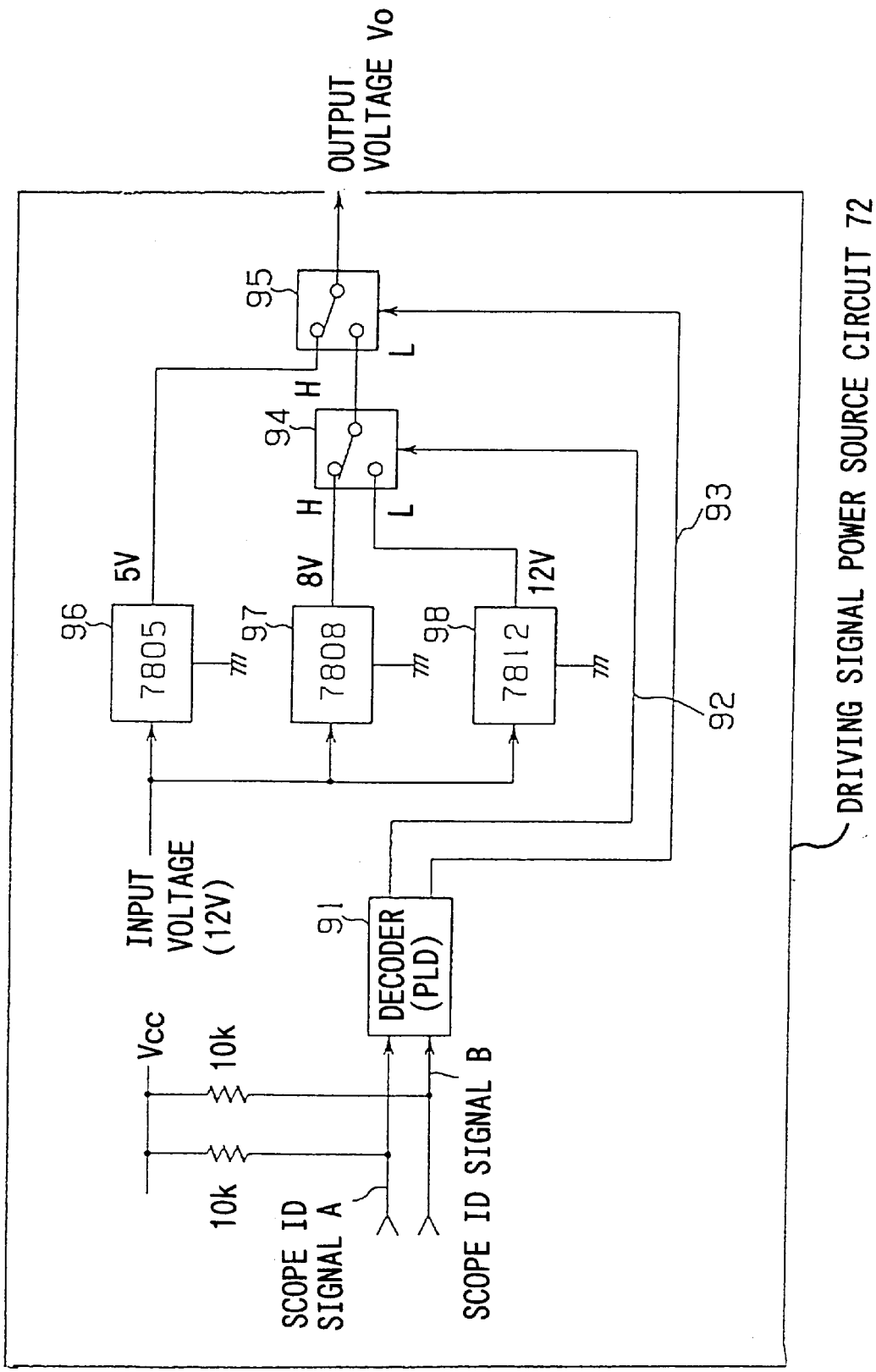
FIG. 10 is a circuit diagram of a driving signal power source circuit of another camera control unit.

As shown in FIG. 10, a driving signal power source circuit 72 uses 2-bits for the scope ID signal including scope ID signal A and scope ID signal B. Each of the input terminals for scope ID signals A and B is connected to $V_{cc}$ via a resistor of 10kΩ and to a decoder 91.

As shown in FIG. 12, both of scope ID signals A and B of video endoscope D are at an "L" level. With respect to video endoscope E, scope ID signal A is at the "L" level and scope ID signal B is at an "H" level. With respect to video endoscope F, scope ID signal A is at the "H" level and scope ID signal B is at the "L" level. When no video endoscope is connected, both of scope ID signals A and B are at the "H" level.

Thus, when a video endoscope is connected to the camera control unit 70, the decoder 91 outputs to A-relay 94 and B-relay 95 via cord A 92 and cord B 93 two outputs corresponding to a combination of two scope ID signals A and B, thereby switching the output voltage $V_o$.

The crest value of the driving signal outputted from the camera control unit 70 is different for the three video endoscopes. Therefore, three regulators corresponding to the respective video endoscopes are provided. First, second, and third regulators 96, 97, and 98 generate voltages of 5 V, 8 V, and 12 V, respectively.

One of the three voltages outputted from the three regulators 96, 97, and 98 is selected by switching A-relay 94 and B-relay 95. The selected voltage is outputted as the output voltage $V_o$.

That is, as shown in FIG. 13, when both of scope ID signals A and B are at the "L" level, "H" level signals are outputted to cord A 92 and cord B 93. Thus, the two relays 94 and 95 turn to the "H" level side so that the output voltage $V_o$ is 5 V.

When scope ID signal A is at the "L" level and scope ID signal B is at the "H" level, an "H" level signal is outputted to cord A 92 and an "L" level signal is outputted to cord B 93. Therefore, A-relay 94 turns to the "H" level side and B-relay 95 turns to the "L" level side so that the output voltage $V_o$ is 8 V.

When scope ID signal A is at the "H" level and scope ID signal B is at the "L" level, "L" level signals are outputted to cord A 92 and cord B 93. Therefore, A-relay 94 and B-relay 95 turn to the "L" side so that the output voltage $V_o$ is 12 V.

When both of scope ID signals A and B are at the "H" level, "H" level signals are outputted to cord A 92 and cord B 93. Thus, A-relay 94 and B-relay 95 turn to the "H" level side so that the output voltage $V_o$ is 5V, as in the case in which both of scope ID signals A and B are at the "L" level.

The decoder 91 is preprogrammed in accordance with the input/output relation shown in FIG. 13.

An operation of the camera control unit 70 so structured will be described.

In the camera control unit 70 of this embodiment, when no video endoscope is connected, both of scope ID signals A and B are at the "H" level and the "H" level signals are outputted to cord A 92 and cord B 93, whereby A-relay 94 and B-relay 95 turn to the "H" level side so that the output voltage $V_o$ is 5V.

Therefore, for example, when video endoscope F is connected to the camera control unit 70, the decoder 91 in the camera control unit 70 receives scope ID signals A and B inputted from the video endoscope F, and after a short time A-relay 94 and B-relay 95 are switched. Until A-relay 94 and B-relay 95 are switched, the driving signal having a crest value of 5 V is inputted to video endoscope F. However, since the voltage of the driving signal is lower than the absolute maximum rated value of the charge-coupled device in video endoscope F, the driving signal does not affect the charge-coupled device.

It is the same when video endoscope D or video endoscope E is connected to the camera control unit 70.

Thus, when no video endoscope is connected to the camera control unit 70, the output voltage of the camera control unit 70 is set to output the driving signal having a crest value of 5 V which is smaller than or equal to the absolute maximum rated values of the charge-coupled devices provided in the three video endoscopes.

When one of the three video endoscopes is connected to the camera control unit 70, the camera control unit 70 receives scope ID signals A and B of the video endoscope. In accordance with these signals, A-relay 94 and B-relay 95 are switched. During the short time until the switching has been performed, the driving signal of 5 V is inputted to the video endoscope.

However, sine the voltage of the driving signal is lower than or equal to the absolute maximum rated value of the charge-coupled device in the connected video endoscope, the charge-coupled device in the video endoscope is never damaged.

Types of video endoscopes which can be controlled by the camera control unit 70 can be increased by increasing the number of bits of the scope ID signal, the outputs from the decoder 91, and the relays operated by the outputs.

Further, the output voltage of the camera control unit 70 when the video endoscope is not connected to the camera control unit 70 can be set to be lower than 5 V. It has the same effect as in the case in which the driving signal is stopped by reducing the output voltage of the camera control unit 70 to 0 V.

This embodiment can be applied to a case in which the video endoscopes have the inserting portions of different lengths, namely the specifications of the video endoscopes themselves are different, although their charge-coupled devices have the same specification. In this way, the charge-coupled devices provided to the video endoscopes can be protected.

Further, even if the signal cables for transmitting the driving signals for the charge-coupled devices incorporated in the inserting portions of the video endoscopes have different characteristics, the charge-coupled devices can be protected just like in the case in which the specifications of the video endoscopes themselves are different.

The present invention is not limited to the above described embodiments. There may also be variations of the embodiments which remain within the scope of the present invention.

What is claimed is:

1. A signal cable for transmitting a plurality of signals and being provided to a video endoscope, the video endoscope having a solid state image pick-up device for picking up an image of an object, the signal cable comprising:

an electrically conductive first signal line formed from a non-shielded line for transmitting a first signal, the first signal having a first characteristic;

an electrically conductive second signal line formed from a non-shielded line for transmitting a second signal, the second signal having a second characteristic being different from the first characteristic;

an electrically conductive third signal line formed from a coaxial cable for transmitting a third signal, the third signal having a third characteristic being different from the first and second characteristics, the coaxial cable for transmitting the third signal providing a shielding function;

an electrically conductive fourth signal line formed from a coaxial cable for transmitting a fourth signal, the fourth signal having a fourth characteristic being different from the first and second characteristics, the coaxial cable for transmitting the fourth signal providing the shielding function; and an outer shield member having an inner surface, the inner surface defining a cavity for inserting the first, second, third and fourth signal lines therethrough, the outer shield member having an electromagnetic shielding characteristic, wherein first and second shielded spaces that are shielded by an inner surface of the outer shield member and outer surfaces of the third signal line and the fourth signal line are formed by inserting the third signal line and the fourth signal line through the cavity of the outer shield member, wherein the first signal line is positioned in the first shielded space, and wherein the second signal line is positioned in the second shielded space.

2. The signal cable according to claim 1, wherein one of the first signal line and the second line supplies an electrical power signal for the solid state image pick-up device.

3. The signal cable according to claim 1, wherein the first signal line and the second signal line supplies electrical power signals for the solid state image pick-up device.

4. The signal cable according to claim 1, wherein one of the first signal line and the second signal line supplies a signal for effectuating an electronic shutter function of the solid state image pick-up device.

5. A signal cable for transmitting a plurality of signals and being provided to a video endoscope, the video endoscope having a solid state image pick-up device for picking up an image of an object, the signal cable comprising:

an electrically conductive first signal line formed from a non-shielded line for transmitting a first signal, the first signal having a first characteristic;

an electrically conductive second signal line formed from a non-shielded line for transmitting a second signal, the second signal having a second characteristic being substantially the same as the first characteristic;

an electrically conductive third signal line formed from a non-shielded line for transmitting a third signal, the third signal having a third characteristic being different from the first characteristic;

an electrically conductive fourth signal line formed from a coaxial cable for transmitting a fourth signal, the fourth signal having a fourth characteristic being different from the first and third characteristics, the coaxial cable for transmitting the fourth signal providing a shielding function;

an electrically conductive fifth signal line formed from a coaxial cable for transmitting a fifth signal, the fifth signal having a fifth characteristic being different from the first and third characteristics, the coaxial cable for transmitting the fifth signal providing the shielding function; and an outer shield member having an inner surface, the inner surface defining a cavity for inserting the first, second, third, fourth and fifth signal lines therethrough, the outer shield member having an electromagnetic shielding characteristic, wherein the first and second signal lines are combined and stranded into a stranded line to form a signal line group, the stranded line having a predetermined stranding pitch, wherein first and second shielded spaces that are shielded by an inner surface of the outer shield member and outer surfaces of the fourth and fifth signal lines are formed by inserting the fourth signal line and the fifth signal line through the cavity of the outer shield member, wherein the third signal line is positioned in the first shielded space, and wherein the signal line group is positioned in the second shielded space.

6. The signal cable according to claim 5, wherein the signal line group transmits a plurality of driving signals corresponding to a vertical transfer characteristic of the solid state image pick-up device.

7. The signal cable according to claim 5, wherein the signal line group transmits a plurality of signals corresponding to a horizontal transfer characteristic of the solid state image pick-up device.

8. The signal cable according to claim 5, wherein each one of the fourth signal line and the fifth signal line transmits signals having frequencies which are higher than frequencies of signals transmitted by the signal line group.

9. The signal cable according to claim 5, wherein one of the fourth signal line and the fifth signal line transmits a plurality of output signals from the solid state image pick-up device.

10. A video endoscope comprising:

a long inserting portion including a distal end portion, the distal end portion having a solid state image pick-up device for picking up an image of an object;

an electrically conductive first signal line coupled to the solid state image pick-up device and formed from a non-shielded line for transmitting a first signal, the first signal having a first characteristic;

an electrically conductive second signal line coupled to the solid state image pick-up device and formed from a non-shielded line for transmitting a second signal, the second signal having a second characteristic being different from the first characteristic;

an electrically conductive third signal line coupled to the solid state image pick-up device and formed from a coaxial cable for transmitting a third signal, the third signal having a third characteristic being different from the first and second characteristics, the coaxial cable for transmitting the third signal providing a shielding function;

an electrically conductive fourth signal line coupled to the solid state image pick-up device and formed from a coaxial cable for transmitting a fourth signal, the fourth signal having a fourth characteristic being different from the first and second characteristics, the coaxial cable for transmitting the fourth signal providing the shielding function; and an outer shield member having an inner surface, the inner surface defining a cavity for inserting the first, second, third and fourth signal lines therethrough, the outer shield member having an electromagnetic shielding characteristic, wherein first and second shielded spaces that are shielded by an inner surface of the outer shield member and outer surfaces of the third signal line and the fourth signal line are formed by inserting the third signal line and the fourth signal line through the cavity of the outer shield member, wherein the first signal line is positioned in the first shielded space and the second signal line is positioned in the second shielded space in order to form a signal cable, and wherein the signal cable is inserted through the long inserting portion to transmit the first, second, third and fourth signals of the solid state image pick-up device.

11. A video endoscope comprising:

a long inserting portion including a distal end portion, the distal end portion having a solid state image pick-up device for picking up an image of an object;

an electrically conductive first signal line coupled to the solid state image pick-up device and formed from a non-shielded line for transmitting a first signal, the first signal having a first characteristic;

an electrically conductive second signal line coupled to the solid state image pick-up device and formed from a non-shielded line for transmitting a second signal, the second signal having a second characteristic being substantially the same as the first characteristic;

an electrically conductive third signal line coupled to the solid state image pick-up device and formed from a non-shielded line for transmitting a third signal, the third signal having a third characteristic being different from the first characteristic;

an electrically conductive fourth signal line coupled to the solid state image pick-up device and formed from a coaxial cable for transmitting a fourth signal, the fourth signal having a fourth characteristic being different from the first and third characteristics, the coaxial cable for transmitting the fourth signal providing a shielding function;

an electrically conductive fifth signal line coupled to the solid state image pick-up device and formed from a coaxial cable for transmitting a fifth signal, the fifth signal having a fifth characteristic being different from the first and third characteristics, the coaxial cable for transmitting the fifth signal providing the shielding function; and an outer shield member having an inner surface, the inner surface defining a cavity for inserting the first, second, third, fourth and fifth signal lines therethrough, the outer shield member having an electromagnetic shielding characteristic, wherein the first and second signal lines are combined and stranded in a stranded line to form a signal line group, the stranded line having a predetermined stranding pitch, wherein first and second shielded spaces that are shielded by an inner surface of the outer shield member and outer surfaces of the fourth signal line and the fifth signal line are formed by inserting the fourth signal line and the fifth signal line through the cavity of the outer shield member, wherein the third signal line is positioned in the first shielded space and the signal line group is positioned in the second shielded space to form a signal cable, and wherein the signal cable is inserted through the long inserting portion to transmit the first, second, third, fourth and fifth signals of the solid state image pick-up device.

* * * * *